(12) United States Patent
Lerestif et al.

(10) Patent No.: US 7,074,920 B2
(45) Date of Patent: Jul. 11, 2006

(54) PROCESS FOR THE SYNTHESIS OF 1,3-DIHYDRO-2H-3-BENZAZEPIN-2-ONE COMPOUNDS, AND TO THE APPLICATION THEREOF IN THE SYNTHESIS OF IVABRADINE AND ADDITION SALTS THEREOF WITH A PHARMACEUTICALLY ACCEPTABLE ACID

(75) Inventors: Jean-Michel Lerestif, Yvetot (FR);
Jean-Pierre Lecouve, Le Havre (FR);
Daniel Brigot, Sainte-Marie-des-Champs (FR)

(73) Assignee: Les Laboratoires Servier, Courbevoie (FR)

( * ) Notice: Subject to any disclaimer, the term of this patent is extended or adjusted under 35 U.S.C. 154(b) by 0 days.

(21) Appl. No.: 11/057,491

(22) Filed: Feb. 14, 2005

(65) Prior Publication Data

US 2005/0227962 A1 Oct. 13, 2005

(30) Foreign Application Priority Data

Apr. 13, 2004 (FR) .................................. 04 03829

(51) Int. Cl.
*C07D 487/00* (2006.01)
(52) U.S. Cl. .................................................... 540/523
(58) Field of Classification Search ................. 540/523
See application file for complete search history.

(56) References Cited

U.S. PATENT DOCUMENTS 4,584,293 A * 4/1986 Reiffen et al. .......... 514/212.06
4,737,495 A * 4/1988 Bomhard et al. ...... 514/212.07

FOREIGN PATENT DOCUMENTS

| EP | 0065229 | 11/1982 |
|----|---------|---------|
| EP | 0109636 | 5/1984 |
| EP | 0161604 | 11/1985 |
| EP | 0204349 | 12/1986 |
| EP | 0292840 | 11/1988 |

OTHER PUBLICATIONS

*French Search Report for French Application No. 04.03829,* Dec. 2, 2004.
*European Search Report for European Application No. 05290382,* Sep. 5, 2005.

* cited by examiner

*Primary Examiner*—Bruck Kifle
(74) *Attorney, Agent, or Firm*—Hueschen and Sage

(57) ABSTRACT

Process for the synthesis of compounds of formula (I):

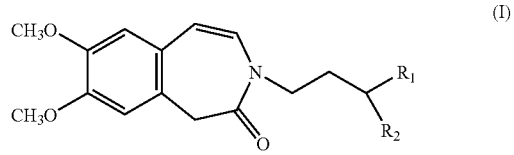

wherein $R_1$ and $R_2$, which may be the same or different, each represent a linear or branched ($C_1$–$C_8$)alkoxy group or form, together with the carbon atom carrying them, a 1,3-dioxane, 1,3-dioxolane or 1,3-dioxepane ring.

Application in the synthesis of ivabradine, addition salts thereof with a pharmaceutically acceptable acid, and hydrates thereof.

11 Claims, No Drawings

PROCESS FOR THE SYNTHESIS OF 1,3-DIHYDRO-2H-3-BENZAZEPIN-2-ONE COMPOUNDS, AND TO THE APPLICATION THEREOF IN THE SYNTHESIS OF IVABRADINE AND ADDITION SALTS THEREOF WITH A PHARMACEUTICALLY ACCEPTABLE ACID

The present invention relates to a process for the synthesis of 1,3-dihydro-2H-3-benzazepin-2-one compounds, and to the application thereof in the synthesis of ivabradine and addition salts thereof with a pharmaceutically acceptable acid.

More specifically, the present invention relates to a process for the synthesis of compounds of formula (I):

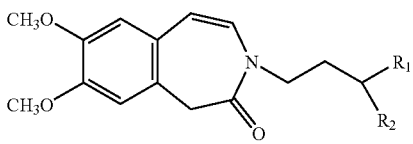

wherein $R_1$ and $R_2$, which may be the same or different, each represent a linear or branched ($C_1$–$C_8$)alkoxy group or form, together with the carbon atom carrying them, a 1,3-dioxane, 1,3-dioxolane or 1,3-dioxepane ring.

BACKGROUND OF THE INVENTION

The compounds of formula (I) obtained according to the process of the invention are useful in the synthesis of ivabradine of formula (II):

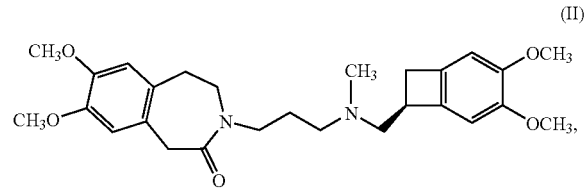

or 3-{3-[{[(7S)-3,4-dimethoxybicyclo[4.2.0]octa-1,3,5-trien-7-yl]methyl}(methyl)amino-propyl}-7,8-dimethoxy-1,3,4,5-tetrahydro-2H-3-benzazepin-2-one, addition salts thereof with a pharmaceutically acceptable acid, and hydrates thereof.

Ivabradine, and addition salts thereof with a pharmaceutically acceptable acid, and more especially its hydrochloride, have very valuable pharmacological and therapeutic properties, especially bradycardic properties, making those compounds useful in the treatment or prevention of various clinical situations of myocardial ischaemia such as angina pectoris, myocardial infarct and associated rhythm disturbances, and also of various pathologies involving rhythm disturbances, especially supraventricular rhythm disturbances.

DESCRIPTION OF THE PRIOR ART

The preparation and therapeutic use of ivabradine and addition salts thereof with a pharmaceutically acceptable acid, and more especially its hydrochloride, have been described in the European patent specification EP 0 534 859.

That patent specification describes the synthesis of ivabradine hydrochloride by starting from the compound of formula (III):

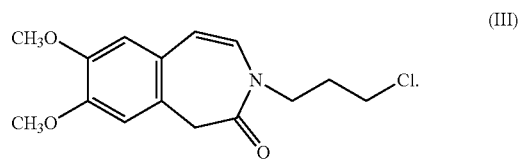

A means of obtaining the compound of formula (III) has been described in the publication J. Med. Chem 1990, Vol. 33 (5), 1496–1504, and also in the patent specification EP 0 204 349, by alkylation of the compound of formula (IV):

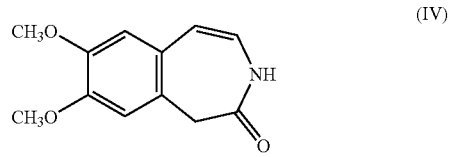

using 1-bromo-3-chloropropane, in dimethyl sulphoxide, in the presence of potassium tert-butoxide.

The patent specification EP 0 204 349 also describes a means of obtaining the diethyl acetal of formula (Ia):

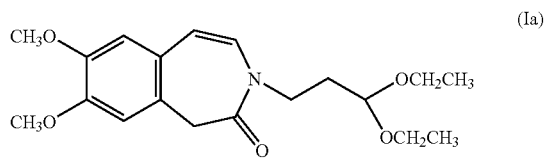

by alkylation of the compound of formula (IV) using the diethyl acetal of 3-chloropropionaldehyde, under the same conditions (potassium tert-butoxide, dimethyl sulphoxide).

The use of a strong base such as potassium tert-butoxide corresponds to the usual conditions required for the deprotonation of an amide function.

However, alcoholates, and especially potassium tert-butoxide, have the disadvantage of being extremely hygroscopic, which complicates their storage and makes them more awkward to use on an industrial scale.

Another reagent often used for the deprotonation of an amide function is sodium hydride, which is used in dimethylformamide.

However, the pairing of sodium hydride and dimethylformamide, besides the fact that it too is highly hygroscopic, has the major disadvantage of being explosive at relatively low temperatures.

Therefore, in view of the industrial value of ivabradine and its salts, it has been imperative to find an effective process especially allowing the 1,3-dihydro-2H-3-benzazepin-2-one compound of formula (I) to be obtained in a good yield whilst avoiding the use of hygroscopic reagents.

DETAILED DESCRIPTION OF THE INVENTION

The Applicant has found that the alkylation reaction of the compound of formula (IV) with a brominated compound could also be carried out in the presence of sodium hydroxide, potassium hydroxide, ammonia in aqueous solution, a carbonate or bicarbonate, especially a carbonate or bicarbonate of sodium, potassium or cesium, the handling of which is much easier, especially on an industrial scale.

This fact is surprising because it runs counter to that which is usually observed in the case of lactams, the deprotonation of which usually requires the use of a stronger base.

More specifically, the present invention relates to a process for the synthesis of compounds of formula (I):

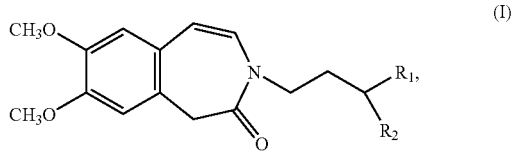

(I)

wherein $R_1$ and $R_2$, which may be the same or different, each represent a linear or branched $(C_1-C_8)$alkoxy group or form, together with the carbon atom carrying them, a 1,3-dioxane, 1,3-dioxolane or 1,3-dioxepane ring, which process is characterised in that the compound of formula (IV):

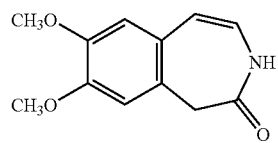

(IV)

is subjected to an alkylation reaction using the compound of formula (V):

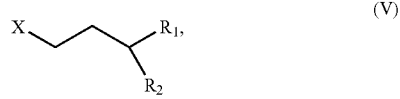

(V)

wherein $R_1$ and $R_2$ are as defined hereinbefore and X represents a leaving group,
in an organic or hydroorganic solvent,
in the presence of a base selected from sodium hydroxide, potassium hydroxide, ammonia in aqueous solution, carbonates and bicarbonates,
to yield, after isolation, the compound of formula (I).

Among the leaving groups there may be mentioned, without implying any limitation, halogen atoms, preferably a bromine atom, and the groups tosylate, mesylate and triflate.

"Hydroorganic solvent" is understood to mean a mixture of water and of an organic solvent.

Among the organic solvents that can be used in the process of the invention, there may be mentioned, without implying any limitation, N-methylpyrrolidone (NMP), dimethylformamide (DMF) and dimethyl sulphoxide (DMSO).

The organic solvent that is preferred for the process of the present invention is N-methylpyrrolidone.

The hydroorganic solvent that is preferred for the process of the present invention is a mixture of water and N-methylpyrrolidone.

The sodium hydroxide and potassium hydroxide can be used in the form of a solid or in the form of aqueous or organic solutions.

When the base is sodium hydroxide, it is preferably used in aqueous solution.

The amount of sodium hydroxide is preferably from 1 to 2 mol per mol of compound of formula (IV).

In the presence of sodium hydroxide, the reaction temperature is preferably from 20 to 100° C.

Preferred carbonates or bicarbonates are sodium, potassium or cesium carbonates or bicarbonates.

In the presence of sodium carbonate or potassium carbonate, the reaction temperature is preferably higher than 80° C.

In the process according to the invention, the compounds of formula (V) preferably used are those wherein $R_1$ and $R_2$ form, together with the carbon atom carrying them, a 1,3-dioxane, 1,3-dioxolane or 1,3-dioxepane ring.

The compounds of formula (I) wherein $R_1$ and $R_2$ form, together with the carbon atom carrying them, a 1,3-dioxane 1,3-dioxolane or 1,3-dioxepane ring are new products which are useful as synthesis intermediates in the chemical or pharmaceutical industry, and as such they form an integral part of the present invention.

The compounds of formula (I) obtained in the process of the present invention are especially useful as synthesis intermediates in the synthesis of ivabradine and addition salts thereof with a pharmaceutically acceptable acid.

By way of example, catalytic hydrogenation of a compound of formula (I) yields the corresponding hydrogenated compound of formula (VII):

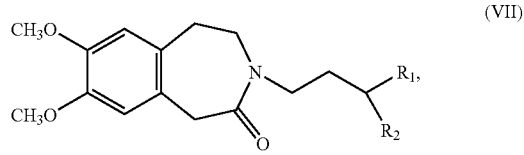

(VII)

wherein $R_1$ and $R_2$ are as defined for formula (I), deprotection of the diacetal of which yields the aldehyde of formula (VIII):

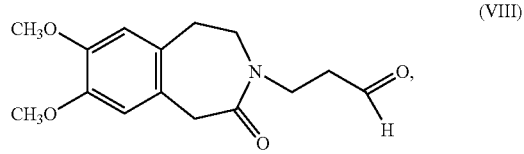

(VIII)

which is reacted with (7S)-3,4-dimethoxybicyclo[4.2.0]octa-1,3,5-trien-7-yl]-N-methylmethanamine under conditions of reductive amination to yield ivabradine.

The Examples hereinbelow illustrate the invention.

EXAMPLE 1

3-[2-(1,3-Dioxolan-2-yl)-ethyl]-7,8-dimethoxy-1,3-dihydro-2H-3-benzazepin-2-one—Procedure in the Presence of Sodium Hydroxide Introduce 100 g of 7,8-dimethoxy-1,3-dihydro-2H-3-benzazepin-2-one, 200 ml of N-methylpyrrolidone and 115 g of 2-(2-bromoethyl)-1,3-dioxolane into a reactor and then bring the temperature of the reaction mixture to 40° C. and add 71 g of 30% sodium hydroxide solution, while maintaining the temperature of the mixture at 40° C. Then heat the mixture at 60° C. and stir for 2 hours; then pour in 400 ml of water at 60° C. and cool the reaction mixture to 20° C. and then, after 1 hour, to 2° C.

Filter off the precipitate obtained, wash it and dry it.

The title compound is obtained in a yield of 87%.

EXAMPLE 2

3-[2-(1,3-Dioxolan-2-yl)-ethyl]-7,8-dimethoxy-1,3-dihydro-2H-3-benzazepin-2-one—Procedure in the Presence of Potassium Carbonate Introduce 100 g of 7,8-dimethoxy-1,3-dihydro-2H-3-benzazepin-2-one, 250 ml of N-methylpyrrolidone and 180.4 g of potassium carbonate into a reactor and then stir the mixture for 3 hours at 130° C. Then add 2-(2-bromoethyl)-1,3-dioxolane on three occasions (90.8 g, 40.7 g and then 16.3 g) at intervals of 2 hours and at 130° C., whilst stirring vigorously.

After returning to ambient temperature, the compound is isolated by precipitation from water, chilling, filtration and drying.

The title compound is obtained in a yield of 80%.

What is claimed is:

1. A process for the synthesis of compounds of formula (I):

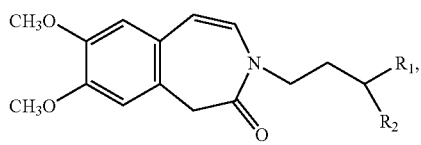

wherein $R_1$ and $R_2$ form, together with the carbon atom carrying them, a 1,3-dioxane, 1,3-dioxolane or 1,3-dioxepane ring,
wherein a compound of formula (IV):

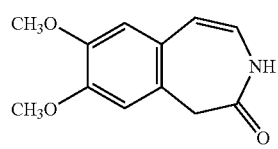

is subjected to an alkylation reaction using a compound of formula (V):

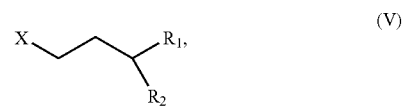

wherein $R_1$ and $R_2$ are as defined hereinbefore and X represents a leaving group,
in an organic or hydroorganic solvent,
in the presence of a base selected from sodium hydroxide, potassium hydroxide, ammonia in aqueous solution, carbonates and bicarbonates,
to yield, after isolation, the compound of formula (I).

2. The process of claim 1, wherein X represents halogen, tosylate, mesylate or triflate.

3. The process of claim 2, wherein X represents bromine.

4. The process of claim 1, wherein the organic solvent is N-methylpyrrolidone.

5. The process of claim 1, wherein the base is sodium hydroxide in aqueous solution.

6. The process of claim 5, wherein the amount of sodium hydroxide is from 1 to 2 mol per mol of the compound of formula (IV).

7. The process of claim 5, wherein the reaction temperature is from 20 to 100° C.

8. The process of claim 1, wherein the base is sodium carbonate or potassium carbonate.

9. The process of claim 8, wherein the reaction temperature is higher than 80° C.

10. A compound selected from those of formula (I):

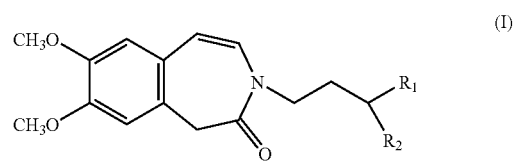

wherein $R_1$ and $R_2$ form, together with the carbon atom carrying them, a 1,3-dioxane, 1,3-dioxolane or 1,3-dioxepane ring.

11. A process for the synthesis of ivabradine, pharmaceutically acceptable salts thereof and hydrates thereof, starting from a compound of formula (I), wherein the compound of formula (I) is obtained according to the process of claim 1, wherein the compound of formula (I) is subjected to catalytic hydrogenation to yield a compound of formula (VII):

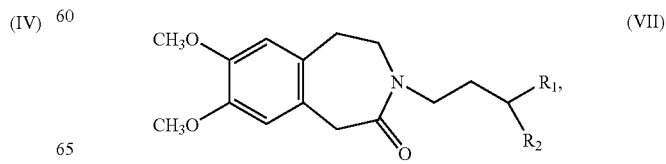

which is subjected to deprotection conditions to yield an aldehyde of formula (VIII):
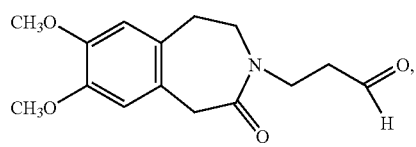
(VIII)
which is reacted with (7S)-3,4-dimethoxybicyclo[4.2.0]octa-1,3,5-trien-7-yl]-N-methylmethanamine under reductive amination conditions to yield ivabradine which is converted, if desired, into a pharmaceutically acceptable salt or hydrate.
* * * * *

UNITED STATES PATENT AND TRADEMARK OFFICE
CERTIFICATE OF CORRECTION

PATENT NO. : 7,074,920 B2  Page 1 of 1
APPLICATION NO. : 11/057491
DATED : July 11, 2006
INVENTOR(S) : Jean-Michel Lerestif et al.

It is certified that error appears in the above-identified patent and that said Letters Patent is hereby corrected as shown below:

Title Page, Item (73), Assignee: "Les Laboratories Servier" should be --Les Laboratoires Servier--.

Signed and Sealed this

Third Day of October, 2006

JON W. DUDAS
*Director of the United States Patent and Trademark Office*